United States Patent [19]

Baker

[11] Patent Number: 4,592,906

[45] Date of Patent: Jun. 3, 1986

[54] ULTRA-VIOLET ABSORBING COMPOUNDS AND COMPOSITIONS CONTAINING SAID COMPOUNDS

[75] Inventor: James A. Baker, Mold, Wales

[73] Assignee: Graesser Laboratories, Ltd., Wales, England

[21] Appl. No.: 699,955

[22] Filed: Feb. 8, 1985

[30] Foreign Application Priority Data

Feb. 14, 1984 [GB] United Kingdom ............. 8403836

[51] Int. Cl.$^4$ .................. A61K 7/44; C07C 101/46
[52] U.S. Cl. ............................... 424/60; 560/19
[58] Field of Search ........................ 560/19; 424/60

[56] References Cited

U.S. PATENT DOCUMENTS 3,390,051  6/1968  Baker et al. .................. 560/19 X

FOREIGN PATENT DOCUMENTS 1064116  4/1967  United Kingdom .

OTHER PUBLICATIONS

Yalkowsky, Design of Biopharmaceutical Properties through Prodrugs and Analogs (1977) 392–408.

*Primary Examiner*—Bernard Helfin
*Attorney, Agent, or Firm*—Cushman, Darby & Cushman

[57] ABSTRACT

2-Ethylhexyl and 2-octyl p-dimethylaminocinnamates unexpectedly are liquid at room temperature and miscible with liquid paraffin (i.e. mineral oil) unlike related alkyl p-dimethylaminocinnamates such as 1-octyl p-dimethylaminocinnamate. They absorb light in the melanogenic range 320 to 420 nm and are dermatologically acceptable and hence useful as UVA absorbers in sunscreen and cosmetic compositions.

10 Claims, No Drawings

ULTRA-VIOLET ABSORBING COMPOUNDS AND COMPOSITIONS CONTAINING SAID COMPOUNDS

The present invention relates to compounds and compositions which absorb ultra-violet radiation in the melanogenic range 320 to 420 nm and has particular, but not exclusive, application to sunscreen and other cosmetic compositions. It provides certain novel esters per se, topical compositions comprising said esters and sunscreening methods.

It is well established that ultra-violet radiation shorter than 320 nm, and especially in the range 280 to 320 nm, is principally responsible for solar erythema (commonly referred to as sunburn). In particular, radiation in the range 280 to 320 nm (the "erythemal" range) penetrates through the corneous and granular cell layers and the underlying network of blood vessels (rete vasculosum) into the papillary layer and exhibits both an erythemogenic and a melanogenic (i.e. pigmentogenic) effect. Radiation of shorter wavelength does not penetrate so deeply and hence is of much lower erythemal effectiveness. Radiation of longer wavelength in the range 320 to 420 nm (the "melanogenic" range) also penetrate into the derma but have a melanogenic rather than an erythemal effect. Accordingly, suntan and the like topical compositions intended to protect against solar erythema whilst permitting tanning of the skin are effective at filtering out erythemal radiation. Compounds for use in such compositions and which absorb radiation in the erythemal range are known in the art as UVB absorbers.

There are circumstances and occasions where it is necessary or desirable to apply to the skin a composition which filters out melanogenic radiation instead of, or, more usually, in addition to erythemal radiation. Excessive tanning is undesirable and can aggravate or cause skin disease and, further, there are some conditions such as photophobia and certain forms of dematitis where melanogenic radiation does cause significant solar erythema. Compounds for use in such compositions and which absorb radiation in the melanogenic range are known in the art as UVA absorbers.

Usually, UVA and UVB absorbers are not applied in their pure state but are dissolved or dispersed in a dermatologically acceptable vehicle which may be aqueous, alcoholic and/or oily. The nature of the vehicle will affect the resistance of the composition to, for example, sweating, swimming and washing. In general terms, it is desirable for UVA and UVB absorbers to be readily incorporated in a range of vehicles and to this end liquids are preferable to solids and, further, good solubility in or miscibility with, organic solvents, especially oils, is desired.

The present inventor believes that all presently known UVA absorbers are solid at room temperature and many have limited solubility in oils. Accordingly, it is an object of this invention to provide a UVA absorber which is liquid at room temperature and is miscible with a wide range of organic solvents, including oils.

It has been disclosed in UK Patent Specification No. 1064116 (published Apr. 5th, 1967 in pursuance of Application No. 13124/63 filed Apr. 3rd, 1983) that compounds of the following Formula A are dermatologically acceptable ultra-violet absorbing compounds which absorb in the melanogenic range

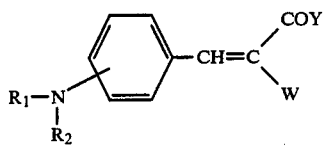
(Formula A)

wherein:
W represents hydrogen or a $-COZ$ group;
Y and Z independently represent $-OB$ or $-OR_3$;
B represents a dermatologically acceptable cationic group;
$R_1$ and $R_2$ independently represent hydrogen, alkyl or aralkyl or together represent an alkylene group optionally interupted by a hetero atom; and $R_3$ represents hydrogen, alkyl or alkoxyalkyl.

The compounds specifically mentioned in the Specification No. 1064116 are the following:
(1) p-dimethylaminocinnamic acid, m.p. 227°–232° C., Formula A: $W=H$, $Y=OH$, $R_1=R_2=CH_3$;
(2) ethyl p-dimethylaminocinnamate, m.p. 70°–72° C., Formula A: $W=H$, $Y=OCH_2H_5$, $R_1=R_2=CH_3$;
(3) isobutyl p-dimethylaminocinnamate, m.p. 60°–63° C., Formula A: $W=H$, $Y=OCH_2CH(CH_3)_2$, $R_1=R_2=CH_3$;
(4) triethanolamino p-dimethylaminocinnamate, m.p. 129°–134° C., Formula A: $W=H$, $Y=ON(CH_2CH_2OH)_3$, $R_1=R_2=CH_3$;
(5) diethyl p-dimethylaminobenzalmalonate, m.p. 111°–112° C., Formula A: $W=COZ$, $Y=Z=OC_2H_5$, $R_1=R_2=CH_3$;
(6) di-isobutyl p-dimethylaminobenzalmalonate, m.p. 99°–100° C., Formula A: $W=COZ$, $Y=Z=OCH_2CH(CH_3)_2$, $R_1=R_2=CH_3$.

A preferred class of compound of Formula A is identified to be the compounds of the following Formula B:

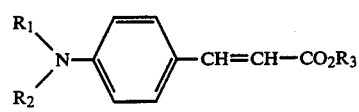
(Formula B)

wherein:
$R_1$ and $R_2$ independently represent $C_1$–$C_4$, especially $C_1$–$C_2$, alkyl; and
$R_3$ represents $C_1$–$C_4$, especially $C_2$–$C_4$, alkyl. It will be appreciated that compounds (1), (2) and (3) referred to above are members of this preferred class.

The present inventor was a co-inventor of the invention claimed in Specification No. 1064116.

As indicated above, all of the compounds of Formula A (and Formula B) specifically disclosed in Specification No. 1064116 are solid at room temperature. Further, recent and unpublished research by the present inventor indicates that the majority of the esters of p-dimethylaminocinnamic acid with commercially available higher alcohols also are solids at room temperature. In particular, the following higher esters are solids:
(a) 3-methylbutyl-p-dimethylaminocinnamate, m.p. 56°–59° C., Formula B: $R_1=R_2=CH_3$, $R_3=-CH_2CH_2CH(CH_3)_2$.

(b) 1-heptyl p-dimethylaminocinnamate, m.p. 41.5°–42° C., Formula B: $R_1=R_3=CH_3$, $R_3=-(CH_2)_6CH_3$.

(c) 1-octyl p-dimethylaminocinnamate, m.p. 48°–48.5° C., Formula B: $R_1=R_2=CH_3$, $R_3=(CH_2)_7CH_3$.

(d) 3,5,5-trimethylhexyl p-dimethylaminocinnamate, m.p. 64°–65° C., Formula B: $R_1=R_2=CH_3$, $R_3=-CH_2CH_2CH(CH_3)CH_2C(CH_3)_3$.

(e) 3,3,5-trimethylcyclohexyl p-dimethylaminocinnamate, m.p. 110° C.,

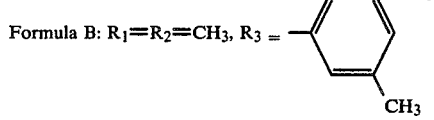

Formula B: $R_1=R_2=CH_3$, $R_3 =$ (f) 1-decyl p-dimethylaminocinnamate, m.p. 50°–51° C., Formula B: $R_1=R_2=CH_3$, $R_3=(CH_2)_9CH_3$.

It has also been observed that the aforementioned higher esters have limited solubility in liquid paraffin (i.e. mineral oil) and hence would be difficult to formulate into oily bases. In particular, their solubilities in liquid paraffin are as follows:

| Ester | Solubility in liquid paraffin at 23 (% wt/vol) |
|---|---|
| (a) $C_5$ (3-methylbutyl) | 2.4 |
| (b) $C_7$ (1-heptyl) | 2.1 |
| (c) $C_8$ (1-octyl) | 2.5 |
| (d) $C_9$ (3,5,5-trimethylhexyl) | 2.9 |
| (e) $C_9$ (3,3,5-trimethylcyclohexyl) | 1.2 |
| (f) $C_{10}$ (1-decyl) | 2.1 |

However, it has been found that, contrary to expectations, two of the octyl esters, namely the 2-ethylhexyl ($R_3=-CH_2CH(C_2H_5)(CH_2)_3CH_3$) and 2-octyl ($R_3=-CH(CH_3)(CH_2)_5CH_3$), of p-dimethylaminocinnamic acid are liquid at room temperature and are completely miscible both with liquid parafin and with methanol. Said liquid esters are believed to be novel compounds.

Accordingly, a first aspect of the present invention provides, as novel compounds per se, 2-ethylhexyl p-dimethylaminocinnamate and 2-octyl p-dimethylaminocinnamate.

Further, a second aspect of the present invention provides a composition for topical application comprising a dermatologically acceptable vehicle containing an effective ultra-violet absorbing amount of 2-ethylhexyl p-dimethylaminocinnamate and/or 2-octyl p-dimethylaminocinnamate.

A third aspect of the present invention provides a sunscreen composition for topical application comprising a determatologically acceptable vehicle containing (a) an effective ultra-violet absorbing amount of 2-ethylhexyl p-dimethylaminocinnamate and/or 2-octyl p-dimethylaminocinnamate and (b) an effective ultra-violet absorbing amount of one or more determatologically acceptable compounds absorbing in the erythemal range 280 to 320 nm.

The expression "dermatologically acceptable" is used herein to indicate not only that the material or compound referred to is acceptable on strictly dermatological grounds, but also that it is acceptable on other physiological grounds, that is to say that if, for example, the material or compound is absorbed through the skin into the bloodstream, it shall not be toxic in the amounts and by the route it is absorbed.

According to a fourth aspect of the present invention, there is provided a method of protecting the skin of an animal (including human) against ultraviolet radiation in the melanogenic range 320 to 420 nm which comprises applying to the skin a coating or film containing an effective ultra-violet absorbing amount of 2-ethylhexyl p-dimethylaminocinnamate and/or 2-octyl p-dimethylaminocinnamate.

As mentioned previously, the novel esters of this invention are liquid UVA absorbers and are completely miscible with both mineral oil and methanol (i.e. right across the polarity spectrum of organic solvents). They are immiscible with water and hence are resistant to removal from the skin by sweating, swimming and washing. Further, their solubility in organic liquids makes it easy to incorporate them in conventional sunscreen and other cosmetic vehicles. If required, they can be directly applied to the skin.

The absorption profiles of the novel esters are similar to those of the lower esters of p-dimethylamino-cinnamic acid disclosed in UK Patent Specification No. 1064116. In particular, maximum absorption is at about 360 nm but the absorptive capacity (as measured at 0.0001% in isopropanol) is lower than that of the corresponding isobutyl ester.

The novel esters can be prepared by conventional methods known per se for the preparation of higher esters. In particular, they can be prepared by (a) ester exchange with a lower ester, (b) condensation of dimethylaminobenzaldehyde with an alkyl acetate, or (c) direct esterification of dimethylamino cinnamic acid.

In the case of ester interchange, a lower alkyl ester of dimethylaminocinnamic acid, especially ethyl dimethylaminocinnamate, is heated with 2-ethylhexanol or 2-octanol in the presence of a base catalyst, especially sodium metal. Preferably, the transesterification is effected at reflux in the presence of a compound having a higher boiling point than the lower alcohol and especially one forming an azeotrope with the alcohol. A suitable azeotrope forming compound is toluene.

In the case of condensation, dimethylaminobenzaldehyde is contacted with an excess of 2-ethylhexyl acetate or 2-octyl acetate in the presence of a condensation catalyst. Suitably, the condensation is carried out by heating the mixture to a temperature of 30° to 100° C. Sodium or potassium alkoxide is the presently preferred catalyst. The sodium or potassium alkoxide can be added to the reaction mixture as such or formed in the reaction mixture from reaction of metallic sodium or potassium, or sodium or potassium hydride, with the corresponding alcohol. There usually is sufficient alcohol present as impurity in the acetate ester for this purpose. Preferably, the acetate is used in sufficient excess to constitute a reaction solvent but a mutual solvent can be employed if desired.

Direct esterification can be carried out by heating, preferably at reflux, a mixture of p-dimethylaminocinnamic acid and 2-ethylhexanol or 2-octanol saturated with hydrogen chloride. Usually, excess alcohol will be used as solvent.

The novel esters of this invention absorb ultraviolet radiation strongly at wavelengths exceeding 320 nm and give a useful measure of absorption up to about 400 nm. Usually, they will be formulated with a dermatologically acceptable liquid or semi-liquid vehicle, for example in the form of a cream or lotion, to provide a composition which on topical application will constitute or leave on the skin a film or coating which will absorb at least a substantial proportion of melanogenic ultra-violet light falling upon it.

Novel sunscreening compositions such as cosmetic oils, alcoholic solutions, lotions, lipsticks, ointments, creams may be prepared with the novel esters. These compositions may be formulated as cosmetic preparations in otherwise conventional fashion. It is preferred that they should be not only dermatologically but also cosmetically or aesthetically acceptable.

Depending on the degree of protection desired and on the vehicle employed, satisfactory results may be obtained with compositions containing from 0.5 to 10% by weight of the novel esters.

Preferably from 1 to 3% by weight is employed although larger amounts may be used if desired. The optimum proportion to employ will depend particularly on the nature of the coating or film formed or left on the skin, since some types of formulation will permit of the formation of a screen of a greater concentration of screening agent per unit of area than others, depending for example on viscosity, spreading power, and the permanence or otherwise of the vehicle or constituents thereof.

The novel sunscreening compositions of this invention are not confined to any particular classes of cosmetics or to any particular formulations. Nevertheless, it is preferred to employ the novel esters with a substantially greater amount of a dermatologically acceptable vehicle compatible with the skin, such as corn oil, aqueous ethanol, isopropanol, sesame oil, propylene glycol, benzyl alcohol, oleyl alcohol, isopropyl esters of fatty acids, such as myristic and palmitic acids, or a mineral oil or wax. The vehicle should be of such a viscosity and/or wetting power that the composition may be satisfactorily applied to the skin as a continuous film or coating, despite the natural oiliness thereof.

The novel sunscreening compositions are applied to the skin in known and conventional manner, normally just prior to the user exposing himself or herself, as the case may be, to the rays of the sun.

According to a particularly preferred embodiment of the present invention, an ultra-violet absorbing composition comprises a dermatologically acceptable vehicle containing (a) as UVA absorber, an effective ultra-violet absorbing amount of 2-ethylhexyl p-dimethylaminocinnamate and/or 2-octyl p-dimethylaminocinnamate and (b) as UVB absorber, an effective ultra-violet absorbing amount of one or more dermatologically acceptable compounds absorbing in the erythemal range 280 to 320 nm.

Suitably, the combined amounts of said UVA and UVB absorbers (a) and (b) is in the range 0.5 to 10% by weight, and most advantageously from 1 to 5% by weight, of the total weight of the composition. The molar ratio of UVA and UVB absorbers one to the other may be, for example, from 1:10 to 10:1, preferably from 5:1 to 1:5 and most advantageously from 2:1 to 1:2.

It is preferred that the UVA and UVB absorbers and the ratio in which they are employed are such that a 0.5% solution of the compounds (taken in that ratio) in a solvent transparent to ultra-violet radiation (for example ethanol) in a layer 1 cm. thick shall reduce the intensity of all radiation between the wavelengths 290 and 400 nm which passes into it by at least 90%.

Presently preferred compounds which may be used as the UVB component of a composition according to the invention are alkyl p-methoxy-cinnamates, especially ethylhexyl p-methoxy-cinnamate; alkyl p-dimethylaminobenzoates, especially ethylhexyl p-dimethylaminobenzoate; and alkoxyalkyl p-methoxycinnamates, especially 2-ethoxyethyl p-methoxycinnamate.

The following Examples are illustrative of the invention. Examples 1 and 2 illustrate the preparation of the novel esters in accordance with the invention, Example 3 is a comparative Example and Examples 4 to 7 illustrate compositions in accordance with the invention.

EXAMPLE 1

2-Ethylhexyl 4-dimethylaminocinnamate

To a mixture of ethyl 4-dimethylaminocinnamate (40 g), 2 ethylhexanol (60 ml) and toluene (60 ml) was added sodium metal (0.1 g). The stirred mixture was heated to 130° and kept at this temperature until ethanol could no longer be detected in the distillate. The mixture was cooled and washed with water. The toluene was removed on a rotary evaporator and the residue fractionated under high vacuum. The main fraction of 2-ethylhexyl 4-dimethylaminocinnamate distilled at 182°–3° C./0.2 mm. It was a pale yellow viscous liquid (38 g) which solidified in the freezing compartment of a refrigerator, and remelted at $-5°$ C. $\lambda$max 360 nm. Equivalent by non-aqueous titration=290 (Theory 291).

EXAMPLE 2

2-octyl 4-dimethylaminocinnamate

Sodium hydride (1.9 g of an 80% dispersion in oil) was added portionwise with stirring over 0.5 hour to 4-dimethylaminobenzaldehyde (7.46 g) in 2-octyl acetate (153 g) at 25° C. The temperature was raised until a steady evolution of hydrogen began (100° C.) and held at this temperature for eight hours. The cooled mixture was treated with glacial acetic acid (4 ml) and then water (50 ml) added. The upper layer was separated, washed with 10% sodium carbonate solution, water, and dried (MgSO$_4$). The excess of 2-octyl acetate was removed by distillation at 15 mm pressure, and the residue fractionated under high vacuum, yielding 7.3 g 2-octyl 4-dimethylaminocinnamate as a pale amber viscous oil, b.p. 194°–200° C./0.25 mm. After freezing it remelted at $-11°$ C.

EXAMPLE 3 (COMPARATIVE)

1-octyl 4-dimethylaminocinnamate

Sodium hydride (1.9 g of an 80% dispersion in oil) was added portionwise with stirring over 0.5 hour to 4-dimethylaminobenzaldehyde (7.46 g) in 1-octyl acetate (158 g) at 25° C. The temperature was raised until a steady evolution of hydrogen was observed (40° C.) and held at this temperature for 48 hours. The cooled mixture was treated with glacial acetic acid (4 ml) and then water (50 ml) added. The upper layer was separated, washed with 10% sodium carbonate solution, water, and dried (MgSO$_4$). The excess 1-octyl acetate was removed by distillation at 15 mm pressure. the residue solidified on cooling. It was crystallised from petroleum ether (B.P. 40°–60°) at 0° C., giving 14.2 g pale yellow crystals, m.p. 48°–49.5° C.

The following 4-dimethylaminocinnamates were prepared similarly: 3-methylbutyl(amyl), m.p. 56°–9° C., 1-heptyl, m.p. 41.5°–42° C., 3,5,5-trimethylhexyl, m.p. 64°–5° C., 3,3,5-trimethylcyclohexyl (homomenthyl) m.p. 110° C., 1-decyl, m.p. 50°–51° C.

EXAMPLE 4

The following ingredients are blended together to form a sun-block oil formulation.

| Ingredient | % w/w |
| --- | --- |
| 2-Ethylhexyl p-methoxycinnamate | 2.0 |
| 2-Ethylhexyl dimethylaminocinnamate | 2.0 |
| 2-Ethylhexyl palmitate | 3.0 |
| Isopropyl myristate | 27.0 |
| Mineral Oil B.P. | 66.0 |
| Perfume | qs |

EXAMPLE 5

A sun-block oil formulation is prepared from the following ingredients.

| Ingredient | % w/w |
| --- | --- |
| 2-Ethylhexyl dimethylaminocinnamate | 2.0 |
| Glyceryl aminobenzoate | 2.0 |
| Isopropanol | 20.0 |
| Multisterol extract | 25.0 |
| Isopropyl palmitate | 51.0 |
| Perfume | qs |

The glyceryl aminobenzoate is dissolved in isopropanol, the remaining ingredients added and mixed well.

EXAMPLE 6

A sun-block lotion as prepared from the following ingredients.

| Ingredient | % w/w |
| --- | --- |
| 1. 2-Ethylhexyl dimethylaminocinnamate | 2.00 |
| 2. 2-Ethylhexyl dimethylaminobenzoate | 2.00 |
| 3. Distilled water | 60.00 |
| 4. Triethanolamine | 0.50 |
| 5. Mineral oil Light | 27.00 |
| 6. Lanolin oil | 3.25 |
| 7. Multisterol extract | 3.00 |
| 8. Cetyl alcohol | 0.25 |
| 9. Stearic acid XXX | 2.00 |
| 10. Preservatives and perfume | qs |

The method of preparation is as follows:
1. Dissolve item 4 in item 3 and heat to 60° C., and add preservative system. (Water phase)
2. Dissolve items 8 and 9 in item 5 at 50° C. Add items 1,2,6 and 7, mix well and heat to 60° C. (Oil Phase)
3. Add oil phase to water phase with thorough mixing and then cool rapidly to below 35° C. Add perfume with mixing.

EXAMPLE 7

A sun-block cream is prepared from the following ingredients:

| Ingredient | % w/w |
| --- | --- |
| 1. Distilled water | 66.00 |
| 2. Mineral oil | 5.00 |
| 3. *Ethoxylated lanolin alcohols | 1.00 |
| 4. **Polyoxyethylene lanolin derivative | 3.00 |
| 5. Glyceryl monostearate | 5.00 |
| 6. Stearic acid XXX | 16.00 |
| 7. 2-Ethylhexyl p-methoxycinnamate | 2.00 |
| 8. 2-Ethylhexyl dimethylaminocinnamate | 2.00 |
| 9. Preservatives and perfume | qs |

*CTFA Adopted Name: Laneth 25
**CTFA Adopted Name: Laneth-10 Acetate.

The method of preparation is as follows:
1. Items 2 to 8 inclusive were mixed together at 75° C. (Oil Phase).
2. The preservative system was dissolved in item 1 and the solution was heated to 75° C. (Water Phase).
3. The water phase at 75° C. was added to the oil phase at 75° C. with mixing. The mixture was then rapidly cooled to below 35° C. when the perfume was added.

EXAMPLE 8

The following ingredients are blended together to form an oil:
White mineral oil: 57.50
Pentaerythritol tetraisostearate: 18.00
Isopropyl myristate: 22.50
2-ethylhexyl-p-dimethylaminocinnamate: 2.00
Perfume: qs.

EXAMPLE 9

A cream is prepared from the following ingredients:

| Oil Phase | |
| --- | --- |
| Coconut oil | 7.00 |
| Lanolin alcohol | 4.00 |
| Stearic acid XXX | 5.00 |
| Glyceryl stearate | 11.50 |
| 2-ethylhexyl-p-dimethylaminocinnamate | 2.00 |
| Water Phase | |
| Water | 67.5 |
| Propylene glycol | 2.0 |
| Triethanolamine | 1.0 |
| Preservative | qs. |

The method of preparation is as follows:
(1) Heat both phases to 75° C.
(2) Add the water phase to the oil phase with stirring.
(3) Continue stirring while cooling to below 50° C.
(4) Add perfume and cool to 35° C. before packing.

EXAMPLE 10

A gel is prepared from the following ingredients:

| Phase 1 | |
| --- | --- |
| Carbopol 3% slurry | 25.00 |
| Water | 22.50 |
| Triethanolamine 10% in water | 7.5 |
| Phase 2 | |
| Isopropanol | 23.00 |
| Propylene glycol | 20.00 |
| 2-ethylhexyl-p-dimethylaminocinnamate | 2.00 |
| Perfume and preservative | qs. |

The method of preparation is as follows:
(1) Disperse Carbopol in water.
(2) Add phase 2, slowly, with stirring.
(3) Add triethanolamine solution and stir until homogeneous.

EXAMPLE 11

The absorptivity of the following p-dimethylaminocinnamate was measured using the formula $$\left(\frac{A(\lambda max)}{c \times b}\right)$$

wherein c is concentration in g/l and b is path length in centimeters:

| Ester | Absorptivity |
| --- | --- |
| 2-Ethylhexyl | 101 |
| 2-Octyl | 95 |
| 1-Octyl | 89 |
| Ethyl | 125 |

$\lambda$max is 363 nm in each case.

I claim:

1. An ester of p-dimethylaminocinnamic acid selected from 2-ethylhexyl p-dimethylaminocinnamate and 2-octyl p-dimethylaminocinnamate.

2. 2-Ethylhexyl p-dimethylaminocinnamate.

3. A composition for topical application comprising a dermatologically acceptable vehicle containing an effective ultra-violet absorbing amount of an ester of p-dimethylaminocinnamic acid selected from 2-ethylhexyl p-dimethylaminocinnamate, 2-octyl p-dimethylaminocinnamate, and mixtures thereof.

4. A composition as claimed in claim 3, wherein the said amount is 1 to 3% by weight of the composition.

5. A sunscreen composition for topical application comprising a dermatologically acceptable vehicle containing (a) as UVA absorber, an effective ultraviolet absorbing amount of an ester of p-dimethylaminocinnamic acid selected from 2-ethylhexyl p-dimethylaminocinnamate, 2-octyl p-dimethylaminocinnamate, and mixtures thereof, and (b) as UVB absorber, an effective ultra-violet absorbing amount of one or more dermatologically acceptable compounds absorbing in the erythemal range 280 to 320 nm.

6. A composition as claimed in claim 5, wherein the said UVA and UVB absorbers are present in a combined amount of 1 to 5% by weight of the composition.

7. A composition as claimed in claim 5, wherein said UVA absorber and said UVB absorber and the ratio in which they are employed are such that a 0.5% solution of the absorbers (taken in that ratio) in a solvent transparent to ultra-violet radiation in a layer 1 cm thick reduces the intensity of all radiation between 290 and 400 nm which passes into it by at least 90%.

8. A composition as claimed in claim 5, wherein the UVB absorber is selected from alkyl p-methoxycinnamates, alkyl p-dimethylaminobenzoates, alkoxyalkyl p-methoxycinnamates, and mixtures thereof.

9. A composition as claimed in claim 8, wherein the UVB absorber is selected from ethylhexyl p-methoxycinamate, ethylhexyl p-dimethylaminobenzoate, 2-ethoxyethyl p-methoxycinnamate, and mixtures thereof.

10. A method of protecting the skin of an animal against ultra-violet radiation in the melanogenic range 320 to 420 nm which comprises applying to the skin a coating or film containing an effective ultra-violet absorbing amount of an ester of p-dimethylaminocinnamate selected from 2-ethylhexyl p-dimethylaminocinnamate, 2-octyl p-dimethylaminocinnamate, and mixtures thereof.

* * * * *